United States Patent
Lin et al.

(10) Patent No.: US 10,251,612 B2
(45) Date of Patent: Apr. 9, 2019

(54) METHOD AND SYSTEM FOR AUTOMATIC TUBE CURRENT MODULATION

(71) Applicant: Carestream Health, Inc., Rochester, NY (US)

(72) Inventors: Yuan Lin, Rochester, NY (US); William J. Sehnert, Fairport, NY (US); Nathan J. Packard, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 15/293,326

(22) Filed: Oct. 14, 2016

(65) Prior Publication Data

US 2018/0040121 A1 Feb. 8, 2018

Related U.S. Application Data

(60) Provisional application No. 62/371,950, filed on Aug. 8, 2016.

(51) Int. Cl.
*A61B 6/00* (2006.01)
*A61B 6/03* (2006.01)
*A61B 5/00* (2006.01)

(52) U.S. Cl.
CPC ............ *A61B 6/032* (2013.01); *A61B 5/0035* (2013.01); *A61B 6/405* (2013.01); *A61B 6/488* (2013.01); *A61B 6/544* (2013.01); *A61B 5/0077* (2013.01)

(58) Field of Classification Search
CPC ....... G06T 7/0002; G06T 15/08; G06T 19/00; G06T 2207/10116; G06T 2200/04; G06T 13/20; G06T 15/205; G06T 7/0012; G06T 7/13; H04N 13/0275; G06K 9/00201; A61B 6/466; A61B 6/5211; A61B 6/5247; A61B 6/482; A61B 6/486
See application file for complete search history.

(56) References Cited

U.S. PATENT DOCUMENTS 4,835,712 A * 5/1989 Drebin .................... G06T 17/00
345/423
5,690,107 A * 11/1997 Hofmann .................. A61B 6/08
378/206
5,867,555 A    2/1999 Popescu et al.
(Continued)

FOREIGN PATENT DOCUMENTS

WO    2016/003957 A2    1/2016

OTHER PUBLICATIONS

J. Geng, "Structured-light 3D surface imaging: a tutorial", Advances in Optics and Photonics, 2011, 3(2), pp. 128-160.
(Continued)

*Primary Examiner* — Manav Seth (57) ABSTRACT

A method for generating a modulation tube current waveform acquires reflectance images of a subject and generates a surface contour characterization of the subject according to the reflectance images. The surface contour is registered to the imaged field of view. A volume image is formed according to the generated surface contour. A modulation factor for the radiographic volume imaging apparatus is determined at a plurality of modulation points. A modulation tube current waveform is generated using the modulation factor.

17 Claims, 8 Drawing Sheets

(56) References Cited

U.S. PATENT DOCUMENTS

| | | | |
|---|---|---|---|
| 6,259,943 B1* | 7/2001 | Cosman | A61B 90/10 600/417 |
| 6,275,562 B1 | 8/2001 | He et al. | |
| 6,314,311 B1* | 11/2001 | Williams | A61B 8/0841 345/7 |
| 6,438,272 B1* | 8/2002 | Huang | G01B 11/2527 356/4.09 |
| 6,674,431 B1* | 1/2004 | Enomoto | G06T 17/00 345/419 |
| 6,937,348 B2* | 8/2005 | Geng | G01B 11/2509 356/602 |
| 7,551,710 B2* | 6/2009 | Abe | G01N 23/046 378/10 |
| 7,558,364 B2* | 7/2009 | Lin | A61B 6/032 378/16 |
| 7,587,023 B2* | 9/2009 | Hur | A61B 6/481 378/110 |
| 7,623,736 B2* | 11/2009 | Viswanathan | G06T 5/50 348/144 |
| 7,689,014 B2* | 3/2010 | Abovitz | A61B 6/022 382/128 |
| 7,844,320 B2* | 11/2010 | Shahidi | A61B 5/06 600/407 |
| 8,130,384 B2* | 3/2012 | Kindlein | A61B 6/08 356/601 |
| 8,139,111 B2* | 3/2012 | Oldroyd | G06K 9/00637 345/619 |
| 8,798,228 B2* | 8/2014 | Chandrashekarappa | A61B 6/032 378/16 |
| 8,965,078 B2* | 2/2015 | Yu | G06T 11/005 382/128 |
| 9,524,552 B2* | 12/2016 | Wang | A61B 6/03 |
| 9,557,158 B2* | 1/2017 | Hofmann | G01B 11/005 |
| 9,795,356 B2* | 10/2017 | Nett | A61B 6/542 |
| 2002/0115923 A1* | 8/2002 | Erbel | A61B 6/541 600/407 |
| 2006/0269165 A1* | 11/2006 | Viswanathan | G06T 5/50 382/293 |
| 2007/0258559 A1* | 11/2007 | Hur | A61B 6/481 378/16 |
| 2008/0095302 A1 | 4/2008 | Ruhrnschopf et al. | |
| 2008/0292149 A1* | 11/2008 | Rasche | A61B 5/1075 382/128 |
| 2009/0244261 A1* | 10/2009 | Maehner | G01B 11/2522 348/46 |
| 2010/0208274 A1* | 8/2010 | Kindlein | A61B 6/08 356/603 |
| 2011/0282181 A1* | 11/2011 | Wang | A61B 5/0095 600/407 |
| 2013/0202079 A1* | 8/2013 | Yu | A61B 6/5258 378/19 |
| 2017/0116762 A1* | 4/2017 | Lin | G06T 11/005 |
| 2017/0196529 A1* | 7/2017 | Lin | A61B 6/527 |

OTHER PUBLICATIONS

M. Ehlke et al., "Fast Generation of Virtual X-ray Images for Reconstruction of 3D Anatomy", Visualization and Computer Graphics, IEEE Transactions, 2013, 19(12), pp. 2673-2682.

F. Remondino et al., "Image-Based 3D Modelling: A Review", in the Photogrammetric Record, 2006, 21(115), pp. 269-291.

M. Geis et al., "Dose Reduction in CT by anatomically adapted tube current modulation", Medical Physics, 1999, 26(11), pp. 2235-2247.

E. Angel et al., "Monte Carlo simulations to assess the effects of tube current", Physics in Medicine and Biology, 2009, 54.3, pp. 497-512.

Commonly assigned U.S. Appl. No. 15/165,159, entitled System and Method for Motion Artifacts Reduction filed May 26, 2016, by Yuan Lin et al.

* cited by examiner

METHOD AND SYSTEM FOR AUTOMATIC TUBE CURRENT MODULATION

CROSS REFERENCE TO RELATED APPLICATIONS

This application claims the benefit of U.S. Provisional application U.S. Ser. No. 62/371,950, filed on Aug. 8, 2016, entitled "METHOD AND SYSTEM FOR AUTOMATIC TUBE CURRENT MODULATION" in the names of Lin et. al, incorporated herein in its entirety.

TECHNICAL FIELD

This disclosure relates, in general, to the field medical imaging, such as, computed tomography (CT), tomosynthesis, cone beam computed tomography (CBCT), low-cost CT, radiography, fluoroscopy, mammography, and the like. In particular, the disclosure relates to a system and method to reduce patient dose by applying automatic tube current modulation technique in the image acquisition process.

BACKGROUND

Figure 1:
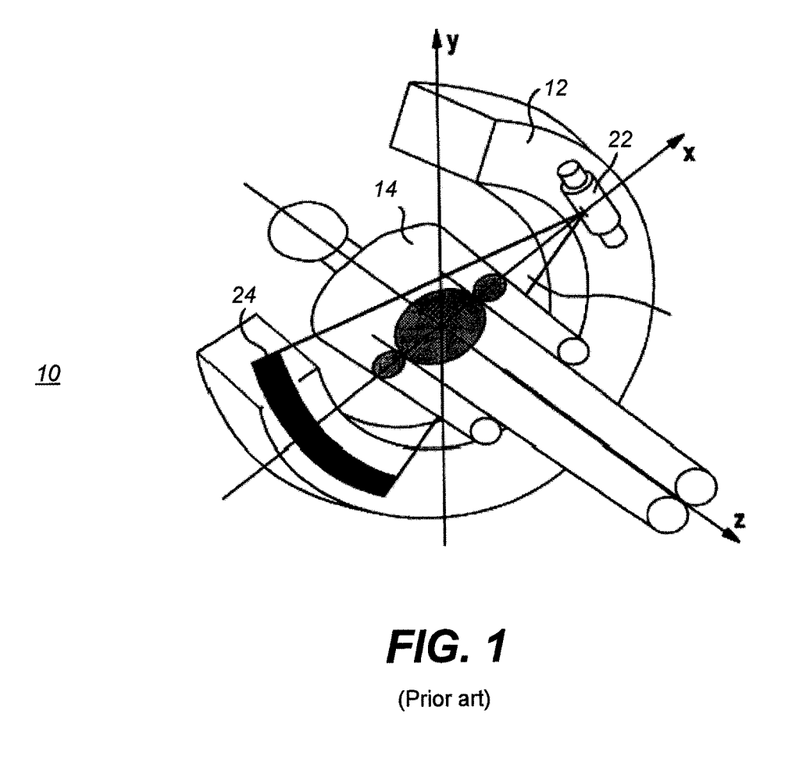
FIG. 1 generally illustrates a CT imaging system used to acquire volume images of a patient.

Computed Tomography (CT) systems and related types of radiographic volume imaging apparatus are known and widely used in various medical and dental applications. See for example U.S. Pat. No. 6,275,562 (He) or U.S. Pat. No. 5,867,555 (Popescu). As illustrated in FIG. 1, a CT imaging apparatus 10 includes an x-ray source 22 that emits an x-ray beam toward one or more detectors 24. In this figure, the x-ray source 22 emits a fan-shaped beam and the detectors 24 are a bank of detectors. Other types of beam shapes (for example, cone beam) and detector shapes (for example, a flat panel detector array) are known. In the system shown in FIG. 1, both source 22 and detector 24 are mounted on a rotational gantry 12 that is actuable to rotate about patient 14. The beam irradiates a slice of patient 14 and the resulting signals at detector 24 channels are sampled by a data measurement system to form a projection data set. Other configurations for CT imaging systems are known, including a number of variants of the basic model shown in FIG. 1. These can include cone-beam CT (CBCT) and multidetector computed tomography (MDCT) apparatus.

Medical x-rays are a valuable tool for diagnosing and treating disease. Along with its benefits, however, there are risks, since the radiation generated by the x-ray system may pose a risk of cancer. To help reduce radiation exposure to the patient, it is desired to acquire diagnostic radiographic images with a low dose, preferably at the lowest possible dose that results in an acceptable diagnostic image.

The relative thickness dimensions and density of the subject anatomy are factors that determine how much radiation energy is needed to obtain suitable image quality from detector 24 data in a radiographic volume imaging apparatus. Across the patient population, there is significant variation in the human body shape, depending on factors such as patient age, sex, height, and weight, for example. In addition, the human body does not conform to ideal geometric shapes or to uniform density or absorption characteristics; there can be significant cross-sectional variation from a cylindrical shape over the patient population. In addition, there are also vast disparities in anatomy density among different body parts (e.g., head vs. chest). Thus, for different patients or body parts, the absorption, scattering, and attenuation of the x-ray beam, and therefore the quantum noise, will vary significantly over a wide range, leading to inhomogeneous noise in the final reconstructed CT images.

Approaches to reducing exposure where possible, based on patient anatomical features include automatic tube current modulation (ATCM) and automatic exposure control (AEC) systems. ATCM and AEC systems have been used with some CT scanners to achieve lower patient dose by adaptively modulating the tube current in the x-y plane (angular modulation) or along the z-axis (z-axis modulation) according to size and attenuation characteristics of the body part being imaged. However, in order to compute tube current at different angles, these methods require obtaining two initial x-ray scout images from orthogonal directions, correspondingly defeating the purpose of ATCM by increasing patient dose. Moreover, existing approaches fail to take into account actual dimensional characteristics of the subject and typically assume that the scanned body part has a uniformly symmetric shape and contour (e.g., circular or elliptical).

The discussion above is merely provided for general background information on some of the problems addressed and is not intended to be used as an aid in determining the scope of the claimed subject matter. The invention is defined by the claims.

SUMMARY

Certain embodiments described herein address the need for methods that adjust radiation exposure for radiographic imaging according to variability in patient anatomy.

To overcome limitations of existing approaches, the present disclosure describes an automatic tube current modulation strategy using a technique that maps the topographic surface of the patient, which in some configurations can be used to automatically determine a better optimized tube current modulation by accurately accounting for the actual shape of the scanned patient, with or without using x-ray scout images.

These aspects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to an embodiment of the present disclosure, there is provided a method for generating a modulation tube current waveform, comprising: acquiring a plurality of reflectance images of a subject; generating a surface contour characterization of the subject according to the plurality of reflectance images; registering the surface contour to the imaged field of view; forming a volume image according to the generated surface contour; determining a modulation factor at each of a plurality of modulation points; and generating a modulation tube current waveform using the modulation factor.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

DETAILED DESCRIPTION OF THE EMBODIMENTS

The following is a detailed description of the embodiments of the invention, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "subject" is used to describe the object that is imaged, such as the "subject patient", for example.

In the context of the present disclosure, "volume image content" describes the reconstructed image data for an imaged subject, generally stored as a set of voxels. Image display utilities use the volume image content in order to display features within the volume, selecting specific voxels that represent the volume content for a particular slice or view of the imaged subject. Thus, volume image content is the body of resource information that is obtained from a radiographic volume imaging apparatus such as a CT, CBCT, MDCT, tomosynthesis, or other volume imaging device that uses a reconstruction process and that can be used to generate depth visualizations of the imaged subject.

Examples given herein that may relate to particular anatomy or imaging modality are considered to be illustrative and non-limiting. Embodiments of the present disclosure can be applied for both 2D imaging modalities, such as radiography, fluoroscopy, or mammography, for example, and 3D imaging modalities, such as CT, MDCT, CBCT, tomosynthesis, dual energy CT, or spectral CT.

In the context of the present disclosure, the term "volume image" is synonymous with the terms "3 dimensional image" or "3D image". In the context of the present disclosure, a radiographic projection image, more simply termed a "projection image" or "x-ray image", is a 2D image formed from the projection of x-rays through a subject. In conventional radiography, a single projection image of a subject can be obtained and analyzed. In volume imaging such as CT, MDCT, and CBCT imaging, multiple projection images are obtained in series, then processed to combine information from different perspectives in order to form image voxels.

In the context of the present disclosure, the equivalent terms "surface contour imaging", "surface contour characterization", or "3D surface imaging" relate to forming a model or image of the surface contour of a subject, characterizing the overall volume of the subject according to its outer surface shape, but not necessarily defining internal features beneath the skin surface. Surface contour imaging techniques include methods that use reflectance images, such as those obtained from reflectance of visible light or near-infrared light from the surface, as described in more detail subsequently. Surface contour imaging algorithms can be used to form a surface model, reconstructed from structured light imaging or from other types of imaging input, typically from reflectance 2D images.

An embodiment of the present disclosure addresses the need for modulating the exposure in a radiographic imaging apparatus using a combination of information that includes surface contour data and anatomy information related to the patient. The described approach can be used for acquiring a single radiographic image from a radiographic imaging apparatus, such as a conventional x-ray system that obtains a single 2D image for viewing, or can be used for acquiring a series of radiographic images needed for reconstructing a 3D volume image from a radiographic volume imaging apparatus, such as with a CT apparatus, for example. The following description is directed to CT scanning, such as scanning a partial or full length of the body of a patient, since this scan procedure can benefit appreciably from tube current modulation as described herein. However, it should be remembered that similar imaging, logic, and control processes to those described for the CT scan can alternately be adapted for use for single-image radiography or for tomosynthesis or other volume imaging types.

Referring again to FIG. 1, CT imaging apparatus 10 provides a helical scan of patient 14, with rotation about a central axis z and translation along axis z. As described previously, gantry 12 provides source 22 and detector 24 that revolve about patient 14, in the axial x-y plane, as gantry 12 translates along axis z.

Used with the system hardware shown in FIG. 1, the method described herein dynamically adjusts the tube current for source 22 according to characteristics of the anatomy for the subject patient. Tube current relates to the number of electron particles that accelerate through the x-ray tube in a given time period. The amount of current then determines the output exposure that is generated by the x-ray tube. That is, radiation dose is proportional to tube current, so that increasing or decreasing tube current increases or decreases radiation dose accordingly. Image noise, meanwhile, is inversely proportional to the square root of the tube current. Thus, lowering tube current can increase image noise.

Applicants describe an Automatic Tube Current Modulation (ATCM) method that uses a Surface Acquisition Technique (SAT) for determining thickness, shape, and overall volume characteristics of the patient and, optionally, also uses personal or statistical information relative to the patient for information on internal skeletal structures of the patient anatomy.

Figure 2:
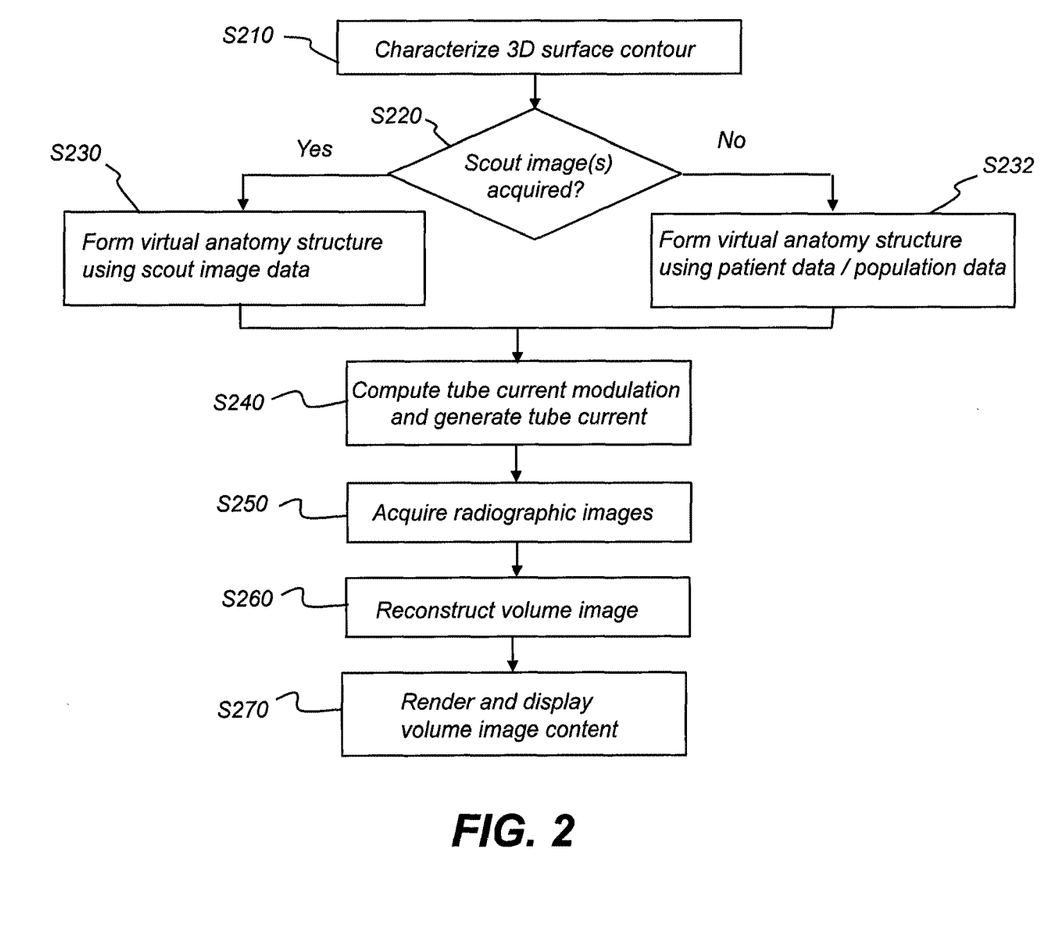
FIG. 2 is a logic flow diagram that shows a sequence for generating a volume image using tube current modulation.

The logic flow diagram of FIG. 2 shows a sequence for image acquisition and processing that uses the tube current modulation approach of the present disclosure. In a surface contour characterization step S210, the surface contour of the subject patient is acquired. Surface contour characterization can be obtained using any of a number of imaging techniques, as described in more detail subsequently. A decision step S220 determines processing flow based on whether or not the imaging system has obtained one or more optional radiographic scout images or scout scans. Where scout images are available, a virtual anatomical structure is formed in a virtual anatomy modeling step S230 according to both the scout image data and the 3D surface contour. Where there are no scout images, the virtual anatomical structure is formed in a virtual anatomy modeling step S232 using the surface contour characterization and other reference information, such as anatomy data from an atlas or other statistically generated model.

Construction of the virtual anatomy model, performed using either step S230 or step S232 of FIG. 2 and described in more detail subsequently, provides the data that can be used to modulate the x-ray tube current appropriately for the patient anatomy that is to be scanned and at each angle and z-axis position. A computation step S240 takes the virtual anatomy model that has been generated and controls the tube current modulation accordingly for each angular and translational z-axis location along the scan path. An image acquisition step S250 then acquires the one or more 2D radiographic projection images needed. For helical CT imaging, for example, the image series can involve a few hundred projection images, each projection image acquired at a different angle and at a different position along the z axis, as shown in FIG. 1. A reconstruction step S260 then performs the needed processing for volume image reconstruction from 2D projection image data. A rendering and display step S270 executes to display a slice or other suitable portion of the generated volume image content.

Surface Contour Acquisition (Step S210)

In order to adjust tube current modulation accurately, the imaging apparatus obtains a surface contour characterization, as described previously with reference to the sequence of FIG. 2. One familiar method for surface contour modeling uses structured light imaging.

Figure 3:
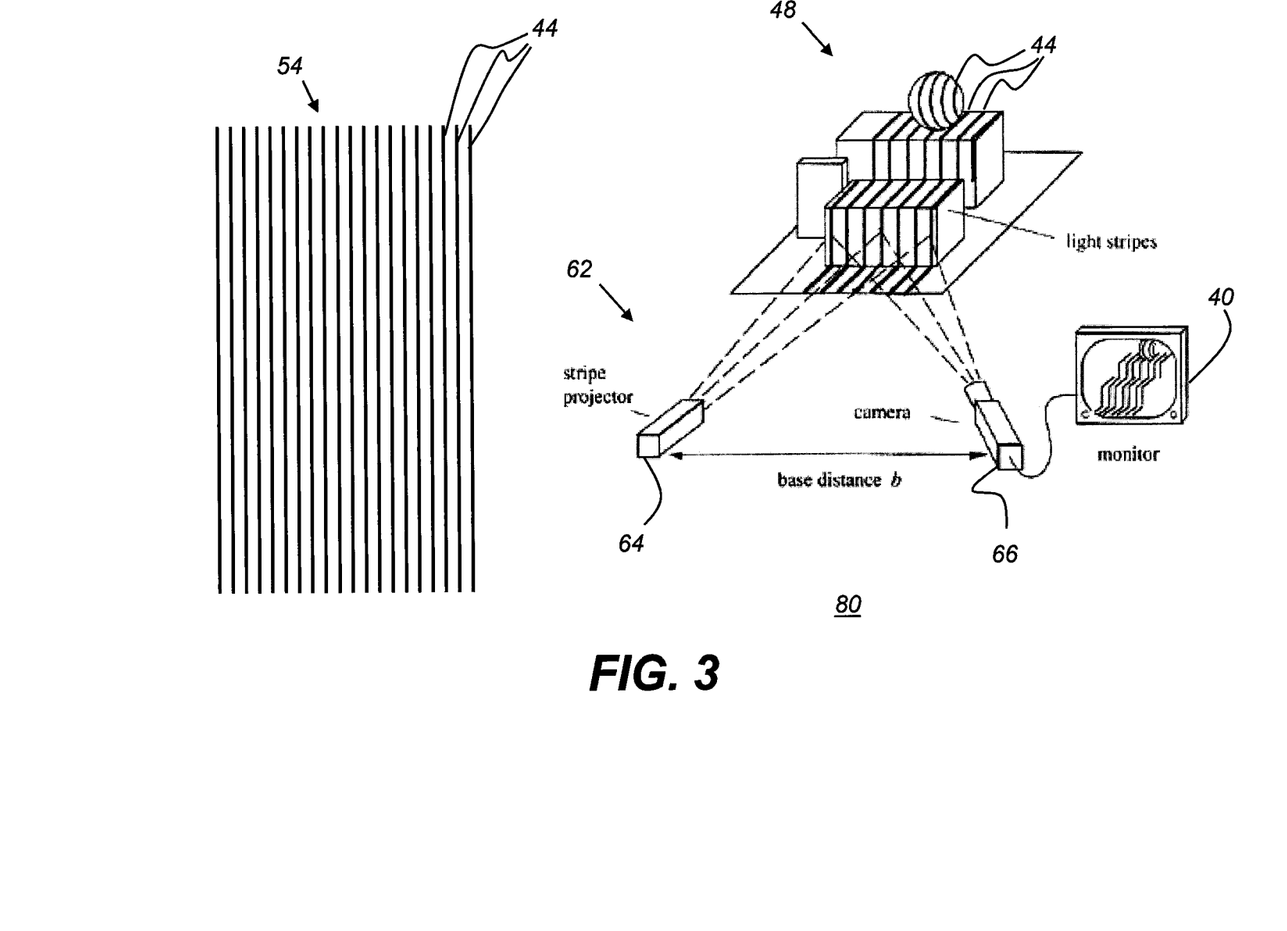
FIG. 3 is a schematic diagram that shows apparatus for contour characterization.

FIG. 3 shows a surface imaging apparatus 80 that uses surface contour acquisition principles, in schematic form. Surface contour acquisition can be provided from a scanner 62 having a projector 64 that directs a pattern 54 of lines 44 or other features individually from a laser source at different orbital angles toward a surface 48, represented in FIG. 3 by multiple geometric shapes. The combined line images recorded by a camera or other type of image sensor 66, from different angles but registered to geometric coordinates of the imaging system, provide structured light pattern information. Triangulation principles, using known distances such as base distance b between camera 66 and projector 64, are employed in order to interpret the projected light pattern and compute contour information to characterize patient anatomy or other surface using the detected line deviation. Lines 44, or other projected pattern, can be visible light or light of infrared wavelengths not visible to the patient and to the viewer, but visible to the appropriate imaging sensors. An optional monitor 40 shows the acquired surface contour as reconstructed by computer processor logic using one or more surface contour reconstruction algorithms.

Other methods for obtaining the surface contour can alternately be used. Alternate methods include stereovision technique, structure from motion, and time-of-flight techniques, for example. The surface contour can be expressed and displayed as a mesh, using techniques familiar to those skilled in the contour imaging arts.

A surface acquisition system or surface imaging apparatus 80 can use a structured light imaging technique, using one or more light sources and one or more light sensors as shown in FIG. 3. The surface acquisition system projects, onto the patient, a known pattern of a light grid using the light sources. The deformed light pattern can be monitored by light sensors and analyzed by a host processor or computer to reconstruct a 3D surface model of the object. An exemplary structured light technique is described in Jason Geng, "Structured-light 3D surface imaging: a tutorial" *Advances in Optics and Photonics*, 2011. 3(2): p. 128-160, incorporated herein in its entirety by reference. Advantageously, 3D surface contour characterization using structured light requires very little time for image acquisition and processing.

Forming the Virtual Anatomy Structure

Steps S230 or S232 in FIG. 2 illustrate forming a virtual anatomy model using the acquired surface contour and other information on internal anatomy structures applicable to the patient. The virtual anatomy model allows a more accurate computation of tube current at each modulation point for obtaining a projection image at each angular and axial position.

As the logic sequence of FIG. 2 shows (Step S230), one or more scout images may be available, showing internal structure of the patient within the field of view of both x-ray imaging and the surface imaging apparatus. Where this information is available, the scout image content, showing internal anatomy and structure from one or more angles, can be registered with the surface contour data to provide an indication of needed exposure for imaging at each location. The scout image shows the amount of bone mass, for example, for various skeletal features that can vary significantly from one patient to the next. A standard bone type or portion, such as from an atlas or other known reference, can be considered as a starting point, then adapted and morphologically adjusted according to the scout image(s).

Alternately, where no scout image is available, other reference information can be used to determine morphology of various internal structures for a particular patient. In some cases, patient data from previous exams is available, allowing a more accurate modeling of internal structures. Alternately, an atlas or statistical information from the patient population can be registered to the surface contour characterization and used to approximate characteristics of the subject to be imaged in order to compute an appropriate modulation factor at each modulation point.

Figure 4A:
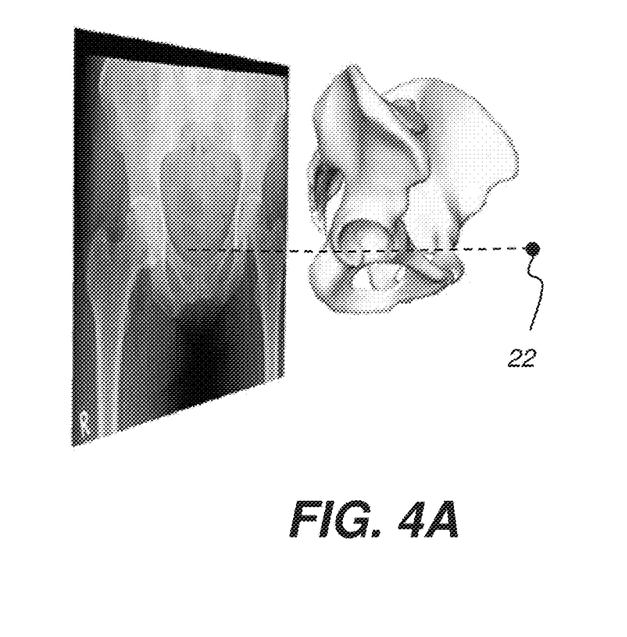
FIGS. 4A-4F show various examples of the results of a deformation process for an anatomical structure.
Figure 4B:
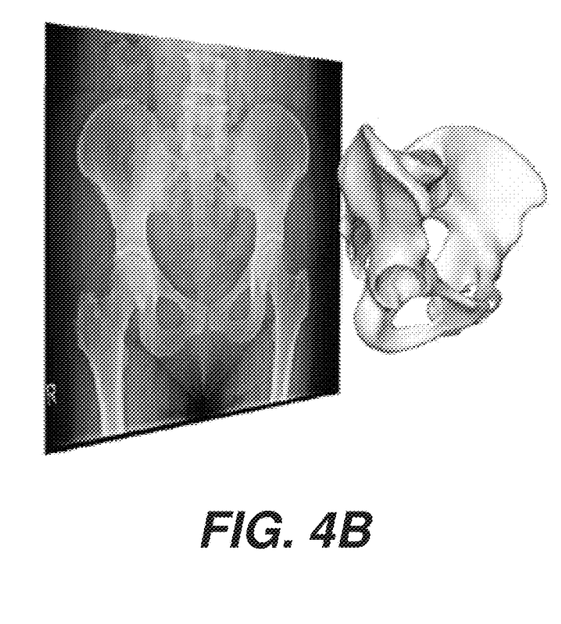
Figure 4C:
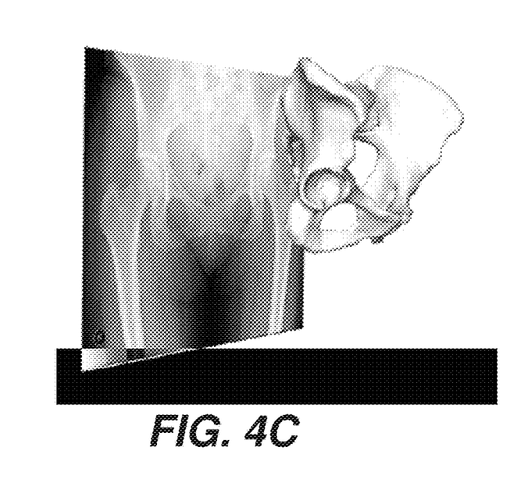
Figure 4D:
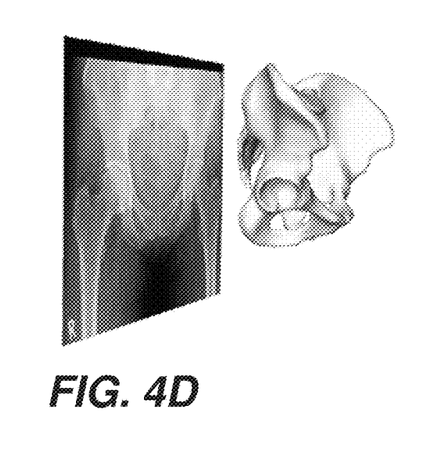
Figure 4E:
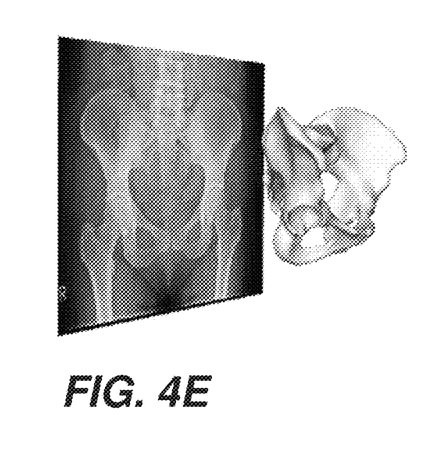
Figure 4F:
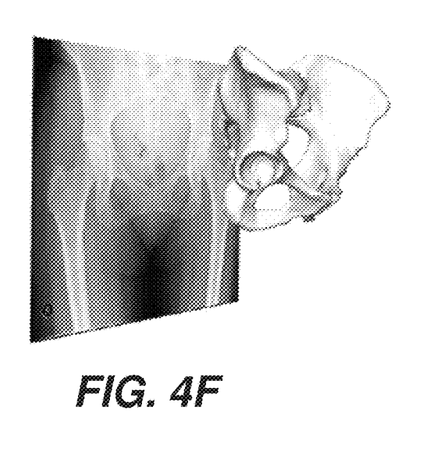

By way of example, FIGS. 4A-4C show modeling of different views of the hip or coxal bone region for different patients, showing a 2D projection to the left and a 3D representation of the corresponding feature to the right. As shown in FIG. 4A, the internal structure data can be used to determine a modulation factor for imaging the anatomy at various angles. FIGS. 4D-4F show modified 3D models with morphology and spatial transform formed according to patient x-ray images. The reconstruction of these pelvic bones can be obtained from standard 2D x-ray images using combined deformation and projection approaches computed using a graphical processing unit (GPU). Silhouettes of reconstruction results can be projected into clinical reference images, affecting the reconstructed shape and density distributions. Various materials or body tissues can be associated with the modeling that forms the virtual anatomy structure.

Reference is made to Moritz Ehlke, et al., "Fast generation of virtual x-ray images for reconstruction of 3D anatomy" *Visualization and Computer Graphics, IEEE Transactions*, 2013. 19(12): p. 2673-2682, incorporated herein by reference in its entirety. Reference is also made to Fabio Remondino and Sabry El-Hakim, "Image-based 3D modeling: a review 2006" in The Photogrammetric Record 21(115):pp. 269-291 (September 2006), incorporated herein by reference in its entirety.

Computing Tube Current Modulation

Figure 5A:
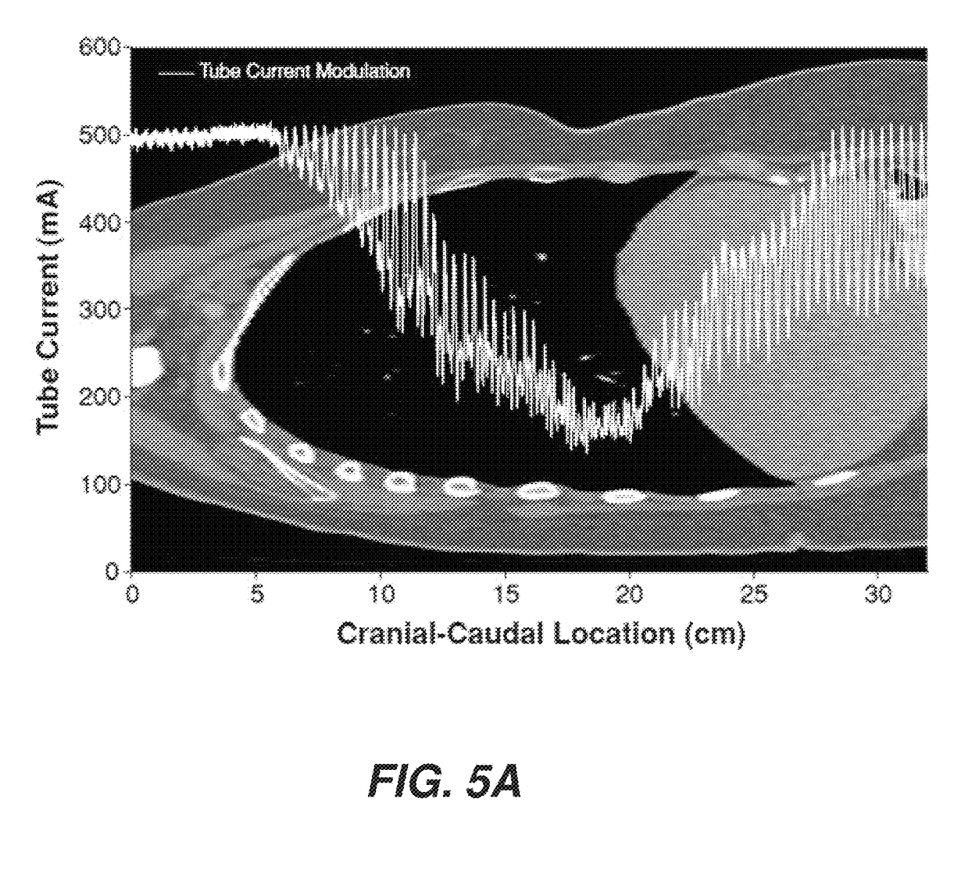
FIG. 5A generally shows an example tube current signal showing modulation according to subject size and density.
Figure 5B:
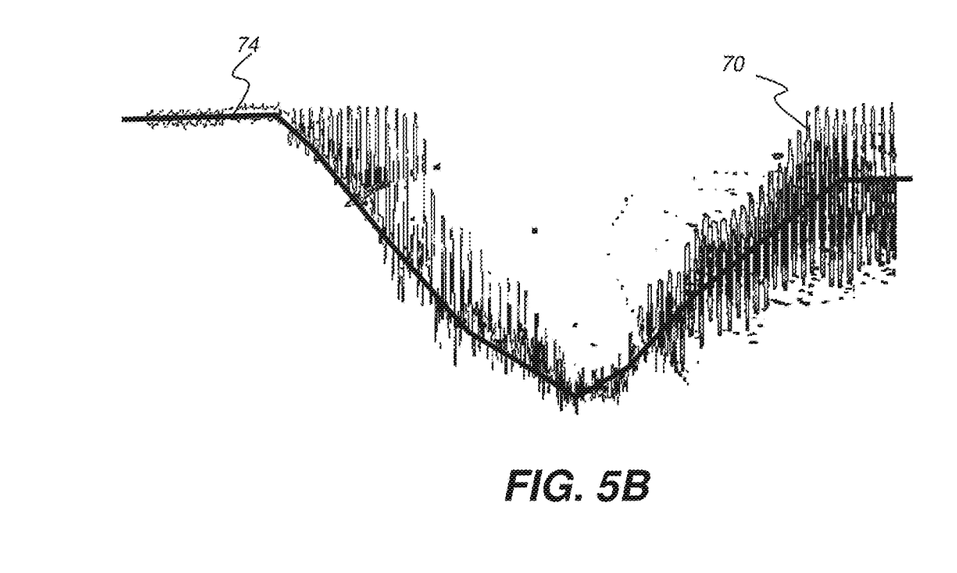
FIG. 5B shows the current modulation signal.
Figure 5C:
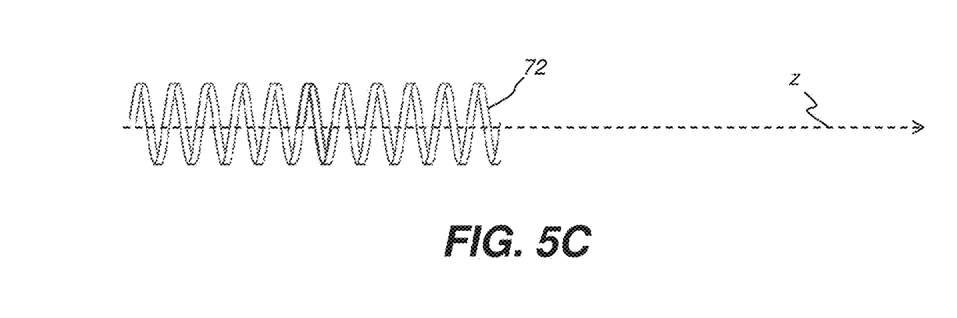
FIG. 5C schematically shows the helical scan pattern for CT imaging.

As shown in the sequence of FIG. 2, an optimized tube current modulation is computed based on the acquired surface contour data and on information about internal structures. FIGS. 5A and 5B show an exemplary tube current modulation signal 70 and its variation at different modulation points. In FIG. 5A, current modulation signal 70 is shown superimposed on a cross-sectional sagittal view of the corresponding patient anatomy. FIG. 5B shows modulation signal 70 without the anatomy background. FIG. 5C shows a helical scan pattern 72 that tracks the orbit of source 22 and detector 24 (FIG. 1) along axis z. Each horizontal position along the graph of FIG. 5B can be considered to represent a modulation point or, using a time base, modulation instant, for the tube current signal. Each acquired radiographic image can be considered to have a corresponding modulation point that relates to angular and linear position relative to the subject. Alternately stated, each rotational angle position and linear z-axis position with respect to the subject as represented in FIGS. 5A-5C can be considered to represent a separate modulation point in terms of varying tube current.

As is shown in FIG. 5A and more pronouncedly in FIG. 5B, a predominant, low frequency "carrier" signal 74, highlighted in bold, shows current variation along the z axis of FIG. 1, changing as a baseline signal according to overall density variation at the corresponding point along the patient's body. This lower frequency signal is modulated by an angular signal of higher frequency from the revolution of the source 22 and detector 24 that varies at each modulation point with the rapidly changing acquisition angle for the helical scan pattern 72. The modulation factor at each angle can differ, causing rapid change in current modulation signal 70 at each modulation point, as shown.

In particular embodiments, the tube current is modulated based on the patient size, shape and density along the longitudinal (z direction) and within the axial (x, y) plane. For thick and/or high density regions, such as the shoulder, the tube current should be high enough to maintain necessary image quality in the reconstructed images; in contrast, for thin and/or low density regions, such as the lungs, tube current can be reduced to avoid unnecessary dose to the patient. With regard to optimizing the tube current modulation, reference is made to Michael Gies, et al., "Dose reduction in CT by anatomically adapted tube current modulation, I. Simulation studies". *Medical Physics*, 1999. 26(11): p. 2235-2247, incorporated herein by reference in its entirety.

Approaches to computing tube current modulation can use any of a number of techniques for determining the dose that provides suitable image quality at each modulation point as source/detector position changes in revolving about the patient.

Reference is made to Angel, Erin, et al. "Monte Carlo simulations to assess the effects of tube current modulation on breast dose for multidetector CT." *Physics in medicine and biology* 54.3 (2009): pp. 497-512, incorporated herein by reference in its entirety.

Accordingly, Applicants have described an automatic tube current modulation method. In particular, Applicants have developed a patient-specific automatic tube current modulation technique that varies the modulation current at each of any number of modulation points as shown in the example waveforms of FIGS. 5A and 5B.

Reference is made to U.S. Ser. No. 15/165,159 titled SYSTEM AND METHOD FOR MOTION ARTIFACT REDUCTION filed May 26, 2016 to LIN et al, incorporated herein by reference in its entirety. This reference describes a system suitable for reconstructing a 3D volume, comprising: (i) a surface acquisition system comprising a light source and an image sensor for characterizing the surface contour of a patient; and (ii) an x-ray imaging system for acquiring x-ray projection data of the patient from a plurality of angular positions. Such a system would be suitable for use with the method described in this disclosure.

Figure 6:
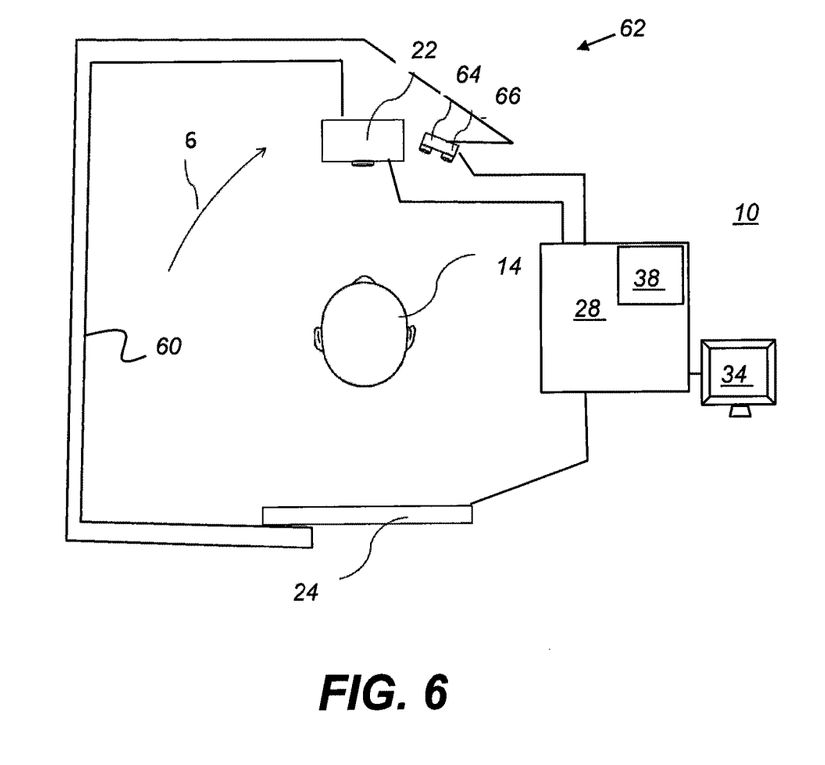
FIG. 6 generally shows an imaging system including a surface acquisition system and an x-ray imaging system.

Referring to FIG. 6, there is shown an imaging apparatus 10 configured for acquiring both surface contour and projection image data for volume reconstruction. As shown, a rotational gantry 60 provides a transport apparatus for orbiting x-ray source 22 and detector 24 about subject patient 14, along with light scanner 62 for surface contour characterization having light pattern projector 64 and camera or sensor 66. A rotation direction 6 is shown. A control logic processor 28 is in signal communication with x-ray source 22, detector 24, and scanner 62 components for surface characterization. Control logic processor 28 can include a controller 38 that coordinates image acquisition between scanner 62 and the radiography apparatus in order to identify and characterize patient motion for control of image acquisition and to support subsequent processing of the x-ray projection image data. Control logic processor 28 can also include the logic for projection image processing and for volume CT image reconstruction as well as surface contour characterization, or may provide connection with one or more additional computers or processors that perform the volume or surface contour reconstruction function and display of volume imaging results, such as on display 34. Such a configuration is suitable for medical and dental applications. For example, a dental imaging device may use CBCT combined with structured light imaging.

In at least one arrangement of the method described in this disclosure, the method includes the steps of:
  i) acquiring a plurality of reflectance images of a subject;
  ii) characterizing a surface contour of the subject according to the plurality of reflectance images;
  iii) registering the surface contour to the imaged field of view;
  iv) forming a volume image according to the surface contour characterization;
  v) determining a modulation factor at each of a plurality of modulation points; and
  vi) generating a modulation tube current waveform.

In a preferred arrangement, the waveform substantially approximates the waveform based on a modulation factor at each of the plurality of modulation points.

In a further step, the generated waveform can be stored, displayed, or transmitted.

In a further step, the generated waveform is applied to an acquisition of one or more x-ray images.

In an optional step, a scout scan of a subject can be acquired to determine the waveform indicative of at least one of subject size and subject shape. With regard to the step of acquiring a plurality of reflectance images of a subject, this can be accomplished by using one or more surface imaging apparatus or by using one or more hand-held surface imaging apparatus, or by using one or more surface imaging apparatus mounted to a rotational gantry of an x-ray imaging system.

With regard to the step of acquiring a plurality of reflectance images of a subject, this can be accomplished by using one or more surface imaging apparatus coupled to a bore of an x-ray imaging system or by using one or more surface imaging apparatus mounted on rails. Alternately, this can be accomplished by using one of a stereovision technique, a structured light technique, a structure from motion technique, and a time-of-flight technique.

With regard to the step of registering the surface contour to the imaged field of view, this can be accomplished by using calibrated world coordinates shared by both the surface acquisition system and the field of view of the x-ray imaging device. For this type of calibration/registration, both devices are registered to the same reference. Registration of the reflectance image content for the surface to the x-ray imaging system can use known geometric relationships of the respective reflectance and x-ray systems, such as where a gantry-mounted reflectance imaging apparatus is used in an x-ray apparatus, for example. Registration of reflectance and radiographic image content can alternately use image content that is perceptible to both the reflectance and radiographic imaging systems. This can include the use of radio-opaque markers or anatomical landmarks, for example, using techniques known to those skilled in the imaging arts.

With regard to the step of registering the surface contour to the imaged field of view, this step comprises one of a forward projection based 2D registration algorithm, a surface-based registration algorithm, a volume-based registration algorithm, a landmark-based registration algorithm, and a curvature-based registration algorithm.

With regard to the step of forming a volume image according to the surface contour characterization, this can be accomplished by assigning a single uniform material/body tissue, a plurality of materials or body tissues, and one or more anatomical structures to the volume image.

With regard to the step of forming a volume image according to the surface contour characterization, this can be accomplished by assigning a plurality of materials/body tissues with anatomical structures from one of an acquired 3D surface model, a reconstructed 3D volume, an organ atlas, and one or more medical images stored in a database. It is noted that the reconstructed volume, organ atlas, and one or more medical images can be CT images, MRI (Magnetic Resonance Imaging) images, ultrasound images, or the like.

With regard to the step of forming a volume image according to the surface contour characterization, this can be accomplished by forming the volume image by cropping, deforming, resizing, stretching, rotating, or reorganizing anatomical structures of medical images stored in a database to match the acquired surface contour.

When a scout scan is acquired, with regard to the step of forming a volume image according to the surface contour characterization, this can further comprise forming the volume image by cropping, deforming, resizing, stretching, rotating, or reorganizing anatomical structures of medical images stored in a database to match a forward projection of a generated volume to the scout scan. This step can further comprise updating the volume image in real-time using the x-ray projection images.

With regard to the step of determining a modulation factor at each of a plurality of modulation points, this can be accomplished by estimating an x-ray signal (for example, as intensity, quality, noise level, and other statistical properties) using deterministic methods (for example, as forward ray tracing) or statistical methods (such as Monte Carlo based methods).

With regard to the step of determining a modulation factor at each of a plurality of modulation points, this can be accomplished by targeting predetermined noise level, image quality of a reference image, reference mAs, reference dose level, or reference contrast-noise-ratio (CNR).

With regard to the step of determining a modulation factor at each of a plurality of modulation points, the plurality of modulation points can comprise one-half of a modulating cycle.

With regard to the step of generating a modulation tube current waveform, this can be accomplished by determining a continuous change of modulation factor of each acquisition point based on a polynomial at each modulation point. Factors for computing this polynomial can include variables related to linear and rotational position for standard patient characteristics, for example.

Consistent with one embodiment, the present invention utilizes a computer program with stored instructions that control system functions for image acquisition and image data processing for image data that is stored and accessed from external devices or an electronic memory associated with acquisition devices and corresponding images. As can be appreciated by those skilled in the image processing arts, a computer program of an embodiment of the present invention can be utilized by a suitable, general-purpose computer system, such as a personal computer or workstation that acts as an image processor, when provided with a suitable software program so that the processor operates to acquire, process, transmit, store, and display data as described herein. Many other types of computer systems architectures can be used to execute the computer program of the present invention, including an arrangement of networked processors, for example.

The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for generating a modulation tube current waveform, comprising:
   acquiring a plurality of reflectance images of a subject;
   generating a surface contour characterization of the subject according to the plurality of reflectance images;
   registering the surface contour to the imaged field of view of a radiographic volume imaging apparatus;
   forming a volume image according to the generated surface contour;
   determining a modulation factor for the radiographic volume imaging apparatus at each of a plurality of modulation points; and
   generating a modulation tube current waveform using the modulation factor.

2. The method of claim 1 wherein the waveform substantially approximates the waveform based on a modulation factor at the plurality of modulation points.

3. The method of claim 1, further comprising storing, displaying, or transmitting the generated waveform.

4. The method of claim 1, further comprising applying the generated waveform to an acquisition of one or more x-ray images.

5. The method of claim 1, further comprising:
   acquiring a scout image of the subject; and
   using the scout image to determine the waveform according to subject size or subject shape.

6. The method of claim 1 wherein the step of acquiring a plurality of reflectance images of the subject comprises at least one of the following:
   (a) using one or more surface imaging apparatus;
   (b) using one or more hand-held surface imaging apparatus;
   (c) using one or more surface imaging apparatus mounted to a rotational gantry of an x-ray imaging system;
   (d) using one or more surface imaging apparatus coupled to a bore of an x-ray imaging system;
   (e) using one or more surface imaging apparatus mounted on rails; and
   (f) using one of a stereovision technique, a structured light technique, a structure from motion technique, and a time-of-flight technique.

7. The method of claim 1 wherein the step of registering the surface contour to the imaged field of view comprises using calibrated world coordinates shared between a surface acquisition device and an x-ray imaging device.

8. The method of claim 1 wherein the step of registering the surface contour to the imaged field of view includes using one of a forward projection based 2D registration algorithm, a surface-based registration algorithm, a volume-based registration algorithm, a landmark-based registration algorithm, and a curvature-based registration algorithm.

9. The method of claim 1 wherein the step of forming a volume image according to the surface contour characterization includes assigning a single uniform material or body tissue, a plurality of materials or body tissues, or one or more anatomical structures to the volume image.

10. The method of claim 1 wherein the step of forming a volume image according to the surface contour characterization includes assigning a plurality of materials or body tissues with anatomical structures from one of an acquired 3D surface model, a reconstructed 3D volume, an organ atlas, and one or more medical images stored in a database.

11. The method of claim 10 wherein the reconstructed volume, organ atlas, and one or more medical images are one of the following: CT images, MRI images, or ultrasound images.

12. The method of claim 1 wherein the step of forming a volume image according to the surface contour characterization includes forming the volume image by cropping, deforming, resizing, stretching, rotating, or reorganizing anatomical structures of medical images stored in a database to match the acquired surface contour.

13. The method of claim 1 further comprising:
   acquiring a scout scan; and
   wherein the step of forming the volume image according to the surface contour characterization comprises: cropping, deforming, resizing, stretching, rotating, or reorganizing anatomical structures of medical images stored in a database to match a forward projection of a generated volume to the scout scan.

14. The method of claim 1 wherein the step of forming a volume image according to the generated surface contour characterization comprises updating the volume image in real-time using the x-ray projection images.

15. The method of claim 1 wherein the step of determining a modulation factor at a plurality of modulation points includes estimating an x-ray signal using deterministic methods or statistical methods.

16. The method of claim 1 wherein the step of determining a modulation factor at a plurality of modulation points includes targeting predetermined noise level, image quality of a reference image, reference mAs, reference dose level, or reference contrast-noise-ratio (CNR).

17. The method of claim 1 wherein the step of generating a modulation tube current waveform includes determining a continuous change of modulation factor for each acquisition based on a polynomial at each modulation point.

* * * * *